(12) United States Patent
Tamayo

(10) Patent No.: US 6,740,078 B2
(45) Date of Patent: May 25, 2004

(54) METHOD AND APPARATUS FOR TREATING PRESBYOPIA

(76) Inventor: Gustavo E. Tamayo, Calle 114 No. 9-45 Torre B Oficina 718, Bogota (CO)

( * ) Notice: Subject to any disclaimer, the term of this patent is extended or adjusted under 35 U.S.C. 154(b) by 252 days.

(21) Appl. No.: 09/841,674

(22) Filed: Apr. 24, 2001

(65) Prior Publication Data

US 2002/0156467 A1 Oct. 24, 2002

(51) Int. Cl.$^7$ .............................................. A61B 18/18
(52) U.S. Cl. .................. 606/5; 606/4; 128/898
(58) Field of Search ................... 606/4, 5, 10, 11; 128/898

(56) References Cited

U.S. PATENT DOCUMENTS

| | | | | |
|---|---|---|---|---|
| 5,196,026 A | * | 3/1993 | Barrett et al. ............... | 623/5 |
| 5,350,374 A | | 9/1994 | Smith ......................... | 606/5 |
| 5,425,727 A | | 6/1995 | Koziol ........................ | 606/5 |
| 5,533,997 A | | 7/1996 | Ruiz ........................... | 606/5 |
| 5,647,865 A | * | 7/1997 | Swinger ...................... | 606/5 |
| 5,754,270 A | * | 5/1998 | Rehse et al. ................ | 351/161 |
| 5,803,923 A | | 9/1998 | Singh-Derewa et al. ...... | 606/5 |
| 5,928,129 A | | 7/1999 | Ruiz ........................... | 600/5 |
| 6,079,417 A | * | 6/2000 | Fugo ........................... | 128/898 |
| 6,129,722 A | | 10/2000 | Ruiz ........................... | 605/5 |
| 6,280,435 B1 | * | 8/2001 | Odrich et al. ............... | 606/5 |

FOREIGN PATENT DOCUMENTS

| | | | | |
|---|---|---|---|---|
| EP | 0201231 A2 | * | 4/1986 | ............ G02C/7/04 |
| WO | WO 99/44492 | | 9/1999 | |
| WO | WO 00/27324 | | 5/2000 | |

* cited by examiner

*Primary Examiner*—Linda C. M. Dvorak
*Assistant Examiner*—Ahmed M Farah
(74) *Attorney, Agent, or Firm*—Gottlieb, Rackman & Reisman, P.C.

(57) ABSTRACT

An apparatus and method are disclosed for treating near vision loss or deficiency, such as presbyopia. In contrast to conventional techniques, a peripheral ablation is provided in an annular zone of the cornea ranging from 5.5 to about 10+ mm to increase the dioptic power of this peripheral zone. The central zone disposed within the peripheral zone of the cornea is left untreated, is corrected for other vision deficiencies or is corrected so that it reverts to its characteristics prior to the peripheral ablation.

11 Claims, 4 Drawing Sheets

ABLATION 100

METHOD AND APPARATUS FOR TREATING PRESBYOPIA

BACKGROUND OF THE INVENTION

A. Field of Invention

This invention pertains to a method and apparatus for treating eye disorders associated with imperfections of a patient's eye and its disability to accommodate for near vision. More particularly, the present invention pertains to a method and apparatus for treatment of presbyopia by shaping an annular or extreme peripheral portion of the patient's cornea to increase its refractive power, preferably using automated laser equipment.

B. Description of the Prior Art

Normally, a sharp image of an object is produced by a person's eye when the image is correctly projected on the retina. The process of focusing the image on the retina is referred to as accommodation, and it describes varying the curvature of the lens to change its focal point. More specifically, objects disposed at distances exceeding a certain threshold (usually about 5 m) are seen clearly by a human eye with no accommodation required and the eye is relaxed. For objects closer than this threshold, the eye must accommodate by squeezing the lens to increase its thickness and change its focal point.

As a person gets older, the lens in his eye and its supporting structure, such as the ligaments or zonules lose elasticity and he slowly loses his ability to accommodate. As a result he can no longer see close objects clearly, i.e., he suffers near vision deficiency. This condition is known as presbyopia.

Until about ten years ago the conventional means of treating presbyopia was by use of positive lenses (in the form of eye glasses or contact lenses). Persons who also had other problems, such as myopia or astigmatism, used negative and cylindrical lenses, respectively. These people had to wear bifocal glasses or contact lenses, i.e., lenses with at least two different portions: a superior portion with one curvature and an inferior portion with another curvature. A person wearing these kinds of lenses has to get used to looking at far objects through the superior portion and looking at close objects (in order of 40 cm or less) through the inferior portion. Eyeglasses are also known with lenses which change gradually from one portion to another so that the lenses have various zones, each zone being optimized for looking at objects within a particular distance range.

Wearing bifocal or multifocal glasses has several disadvantages. One disadvantage is that some persons can get dizzy from such glasses and in fact they can never get used to them. These people normally have two kinds of glasses: one for near vision and another for distant vision. Another disadvantage is that many people find glasses cosmetically unacceptable.

Contact lenses are generally more acceptable cosmetically then glasses. However it is difficult to make bi- or multifocal contact lenses and so at present as presbyopia sets in, some people with contact lens must resort to glasses as well for near vision.

Recently, new techniques have been developed that use lasers to change the optical characteristics of the cornea. Typically, these methods consist of reshaping the cornea by steepening portions thereof. Some methods and apparatus for performing laser surgery on the eyes are disclosed for example in U.S. Pat. Nos. 5,350,373; 5,425,727 6,129,722 and PCT Publication WO 00/27324 all incorporated herein by reference. All these reference disclose methods and apparatus for corrective eye surgery, such as presbyopia, in which a laser beam is directed at the cornea and an ablation is performed to remove material from the cornea thereby changing its optical transmission characteristics. These procedures are performed using one of two techniques. The first technique involves producing an ablation of the cornea in a central zone thereof. The central zone has a diameter in the range of 1.0 –3.0 mm and the ablation causes the central zone to steepen thereby increasing its refractive power. This technique is based on the underlying theory that the central zone of the eye is used for close vision while a peripheral zone of the cornea is used for distant vision. This theory is attributed to the fact that the pupil of the eye is closed by a sympathetic reflex when the person looks at objects located closer than 40 cm. According to this theory, since the pupil opens or dilates for distant objects, the annular portion of the cornea must be used to see far objects.

In other words, some present laser surgical techniques are based on a theory that categorizes the cornea into two zones: a central zone of about 1.0 –3.0 mm that is used for near vision (for objects up to 40 cm); and an annular zone extending from 3.0 mm that is used for distant vision. Based on this theory, for each type of vision problem, the eye of a person is corrected by ablating the appropriate zone without modifying the other zone. More specifically, according to this theory, presbyopia is treated by steeping only the zone extending from 1.0 to 3 mm of the cornea to augment the convergence power of this zone, thereby focusing close objects onto the fovea.

According to the second theory the mulitfocality of the central zone of the cornea is used to view objects at different distances. Accordingly, presbyopia can be corrected by partitioning the central zone of the eye into several regions, ablating these regions independently to obtain different curvatures, each curvature defining a different dioptic powers for the respective region. The multifocality thus obtained may be achieved by excimer laser ablation with tissue being removed from the central zone of the cornea at different depths for each optical region. A person can then use each of the regions to look at objects at corresponding ranges including near vision.

OBJECTIVES AND SUMMARY OF THE INVENTION

In view of the above, it is an objective of the present invention to provide a method and apparatus for treating eye disorders which are more effective then conventional methods and techniques.

A further objective is to provide an improved method which does not require expensive or difficult modifications to the existing eye treatment apparatus.

Yet a further objective is to provide an eye treating method and apparatus which can be adapted easily to treat different eye disorders using the novel as well as conventional techniques.

Other objectives and advantages of the invention shall become apparent from the following description.

The inventors have discovered that contrary to the theories described above, the central zone of the cornea defined as the pupillary area is used by the eye for distant vision while the peripheral zone of the cornea is used for near vision. More specifically, the inventors believe that near vision is produced by light passing through an annular zone extending between 5 –10 mm or more of the cornea, said annular zone being disposed concentrically around the pupil. The remaining central zone of about 5.5 mm is used by the eye for distant vision.

Accordingly, the inventors believe that any corrective surgery for the treatment of near vision, such as presbyopia should be performed in this annular zone, increasing the light that passes through the pupil and improving the intermediate and near vision. The inventors further believe sometimes that during the treatment of the peripheral zone of the cornea for near vision, the optical characteristics of the central zone of the cornea may also change. However, in patients who do not suffer from poor distant vision, such a change is undesirable. Therefore, as a secondary procedure, after the peripheral zone is corrected for near vision, the central zone or pupillary area is also corrected to neutralize any undesirable optical changes in the central portion of the cornea that may have occurred as a result of the peripheral ablation.

The amount of material removed from the cornea for ablation, the optical characteristics of the patient may be considered. For example, for patients having a large pupil, steeper cornea or deeper anterior chamber, less tissue resection is needed and the corneal periphery. For older patients, more tissue resection is needed.

DETAILED DESCRIPTION OF THE INVENTION

Figure 1A:
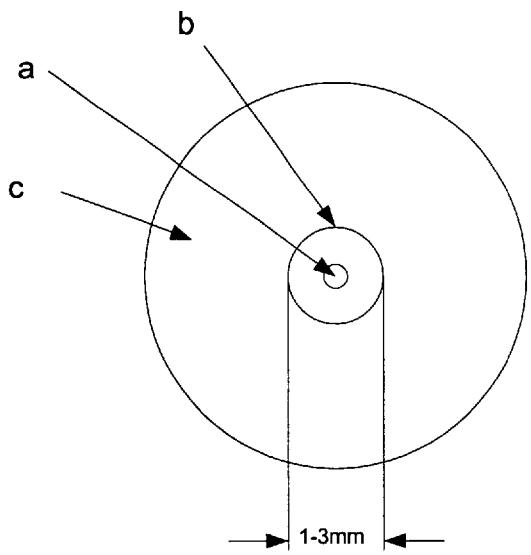
FIG. 1A shows a plan view of a person's cornea indicating a central zone thereof that is subjected to near vision treatment in accordance with conventional techniques.
Figure 1B:
FIG. 1B shows a somewhat enlarged cross sectional profile of the central ablation performed by conventional techniques to treat a near vision deficiency.

Referring first to FIG. 1A, as mentioned above, prior to the present invention it was believed that for near vision the eye makes use of light entering the cornea through a central zone b having a diameter of about 3 mm. Accordingly, most prior art techniques consist of ablating tissue at various depths in the cornea in a central zone b extending between 1 mm and about 3 mm. A small spot of about 1 mm is not ablated. More importantly, the annular zone c extending from about 5 mm to 10+ mm is not substantially ablated during this treatment. FIG. 1B shows a typical prior art profile resulting from central ablation. As can be seen in this profile, the central ablation is concentrated in the vicinity of the outer edge of zone b, i.e., at about 3 mm.

Figure 2A:
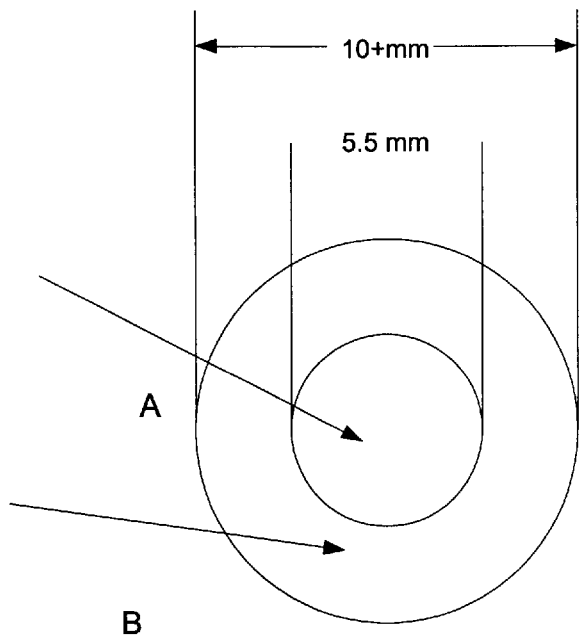
FIG. 2A shows a plan view of a person's cornea indicating an annular zone thereof that is subjected to near vision treatment in accordance with the present invention.
Figure 2B:
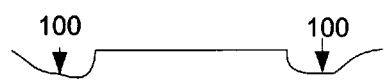
FIG. 2B shows a somewhat enlarged cross sectional profile of the peripheral ablation for near vision treatment of the cornea performed in accordance with the present invention.

According to the present invention, the treatment should not be applied to the central zone of the cornea but to its outer peripheral zone. FIG. 2A shows a schematic view of the cornea with a central zone A of about 5.5 mm and an annular or peripheral zone B extending from 5.5 mm to 10+ mm. A typical profile 100 resulting from peripheral ablation in this peripheral zone B is shown diagrammatically in FIG. 2B. This ablation profile 100 is selected to steepen at least a portion of this peripheral zone B and correct the near vision of the patient for presbyopia and other near vision deficiencies. The size and shape of this ablation profile 100 is determined using standard techniques well known in the art and will not be discussed in detail, however in making the ablation the following patient characteristics are relevant:

A. The pupillary size. An important advantage of the present invention is that a high refractive power peripheral cornea is obtained that allows more light to enter through the pupil. Therefore the pupillary size of the patient is considered when deciding the depth of the peripheral ablation.

B. The preoperative corneal curvature. The flatter the cornea is the deeper the treatment is required in order to achieve the desired level in which the peripheral power of the cornea corrects the presbyopia.

C. The anterior chamber depth. This amount of light entering through the pupil is also dependent on the distance between the pupil and the peripheral cornea, where the ablation is performed. Therefore this distance is also be considered.

Figure 2C:
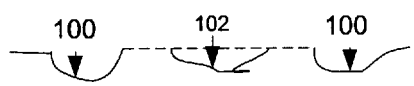
FIG. 2C is similar to FIG. 2B but it also shows an additional central ablation performed in accordance with the present invention.

During peripheral ablation, the central zone A of the cornea is not subjected to any substantial treatment. However, during peripheral ablation, the optical characteristics of the central zone A may also change. Therefore, during, or preferably after the peripheral ablation resulting in profile 100, central ablation is applied to the central zone A to restore the vision of the patient through this central zone to what it was prior to the ablation profile 100. FIG. 2C shows the profile 102 of the ablation applied to the central zone A. As discussed above, the inventors believe that this central zone A is responsible for distant vision which may be normal in a patient with presbyopia. Alternatively, if the patient suffers from poor distant vision as well, and/or has other visual problems the ablation profile 102 may be shaped to correct these problems. It should be understood that in FIGS. 2B and 2C the profiles 100 and 102 are shown schematically only to illustrate the approximate positions of these ablations and not necessarily their actual shape or size.

Figure 3:
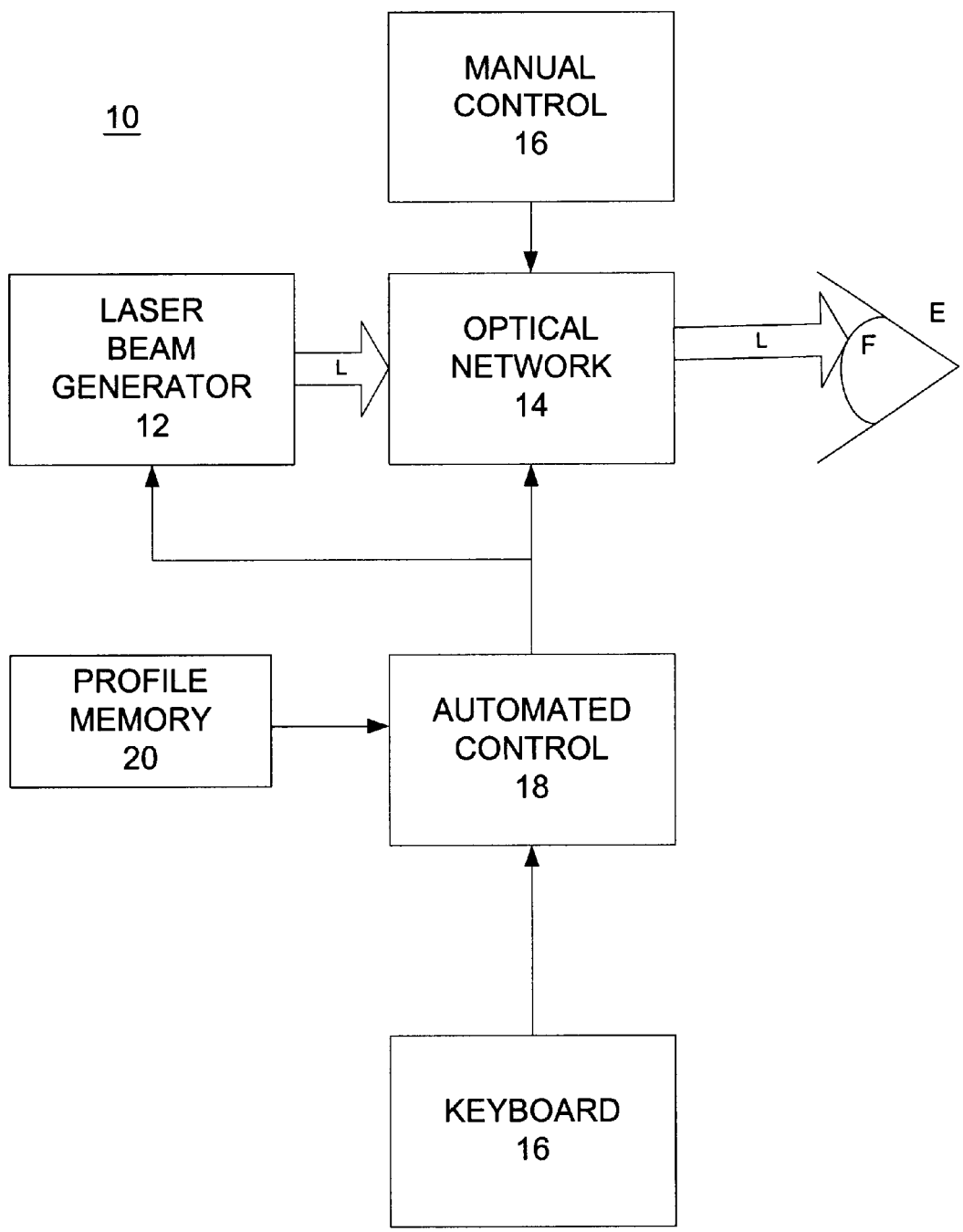
FIG. 3 shows a block diagram for a laser apparatus used to provide treatment in accordance with this invention.

FIG. 3 shows a block diagram for an apparatus 10 arranged and constructed to perform the near vision treatment. The apparatus 10 may be adapted to perform either LASIK or PRK type of surgery. The apparatus 10 includes a laser beam generator 12 which generates a laser beam L. The laser beam generator 12 may be an excimer or a solid state laser generator.

The laser beam L can be a broad beam, a scanning beam or a flying spot type beam and is directed by an optical network toward the eye E of a patient. The network may be manually adjusted using a manual control 14 to insure that the beam L is focused and directed properly on the cornea F.

The apparatus further includes a keyboard 16, an automated control 18 (which is preferably is a microprocessor-based control) and a profile memory 20. The keyboard 16 is used to enter various information about the patient and the surgical operation that is to be performed. Based on this information and other parameters programmed into it, the automated control selects an appropriate profile for the ablation to be performed. In other word, the automated control 18 relies on software to direct the laser beam precisely and determine the movements required to obtain the correct ablation depth, the number of zones for ablation and the diameter of ablation. A set of profiles for various vision problems may be stored in the profile memory 20 and the automated control 18 can access and retrieve these profiles as required. The automated control also operates the laser beam. The apparatus shown in FIG. 3 may be implemented using laser equipment from Autonomous Technology, VISX (Star 2 and Star 3), Laser Sight, Weavelight, Alegretto, Schwind, Bausch and Lomb, Keracor and Meditech Aesculap.

Figure 4:
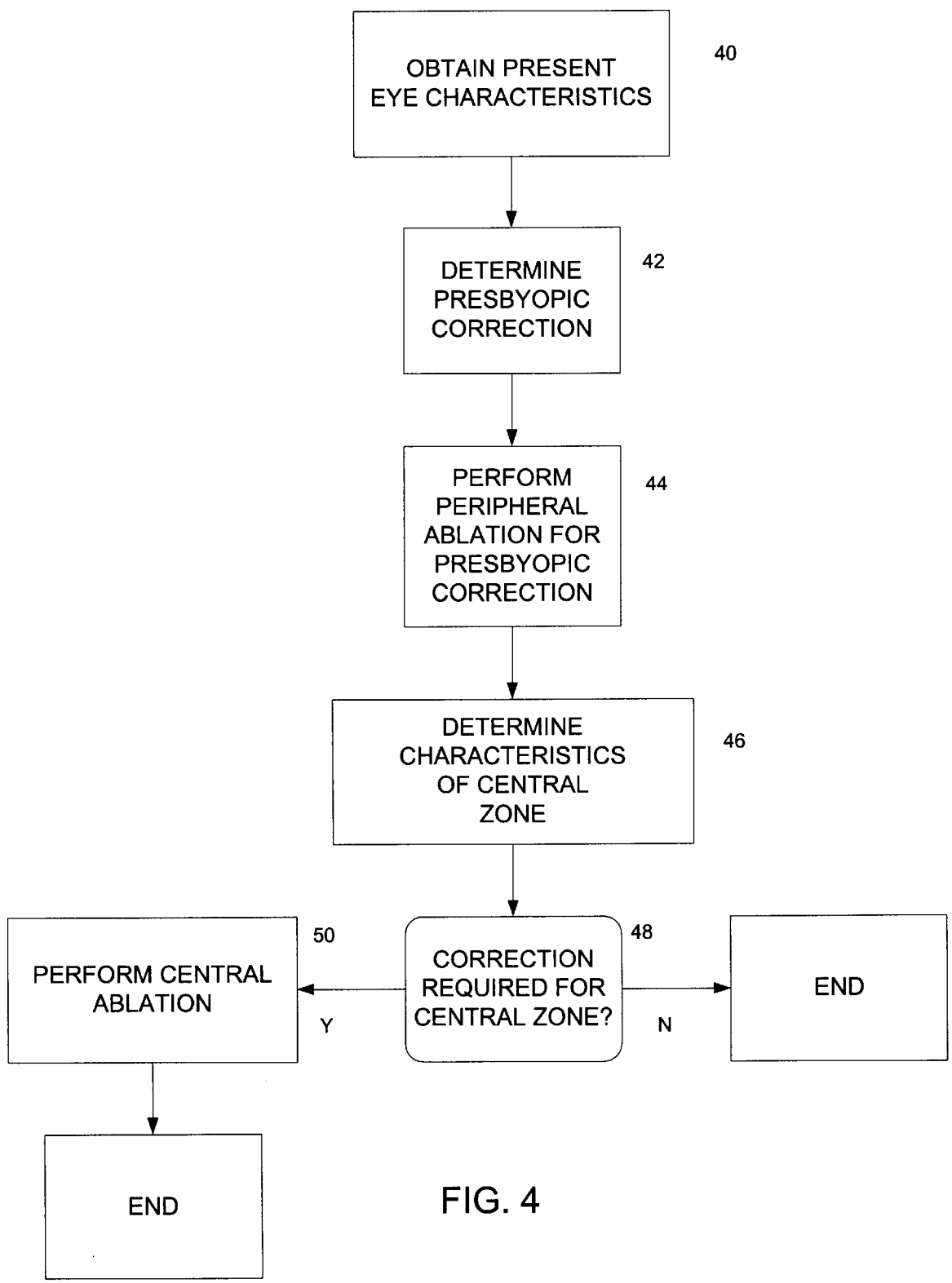
FIG. 4 shows a flow chart for the operation of the apparatus of FIG. 3.

The procedure for performing ablation on a specific patient using the apparatus of FIG. 3 is now described in conjunction with the flow chart of FIG. 4. In step 40, the patient is examined to determine his current eye condition. For example a 55-year old male was found to have plano distant vision and presbyopia. Next, in step 42 it was determined that the treatment for patient's presbyopia required a +2.50 spherical diopter correction. As part of this determination, a complete optometric and ophthalmological examination is performed on the eye, including measurement of the corneal curvature, pupillary size, anterior chamber depth, topography map and ultrasound pachymetry. This information was fed to the automated control 18 which then determined the corresponding ablation profile required to generate the +2.5 spherical diopter correction. In step 44 the ablation process was initiated and the automated control performed the necessary peripheral ablation on the cornea of the patient. Since the +2.5 diopter correction is rather drastic, in step 44 the peripheral ablation profile was performed in two phases. A peripheral ablation of +1.5 spherical diopters was performed in the optical zone B from 6.0 to 9.0 mm. Then a second peripheral ablation of +1.50 diopters was performed in the optical zone B from 5.5 to 9.0 mm. The peripheral ablations are performed on the stromal tissues of the cornea.

As discussed above, a peripheral ablation of the cornea may adversely affect the central zone of the cornea. Therefore, in step 46 the optical characteristics of the eye are checked again. In step 48 a determination is made as to whether a correction is necessary for the central zone. For the subject patient, such a correction was necessary. Therefore, the apparatus of FIG. 3 was used to perform a central ablation to restore the optical characteristics of the central zone A. More specifically, in step 50 a central ablation of 42 microns centered on the pupil was performed. If the patient suffers from other visual impairments, such as hyperopia, additional or other treatment may be applied during this step 50.

Figure 5:
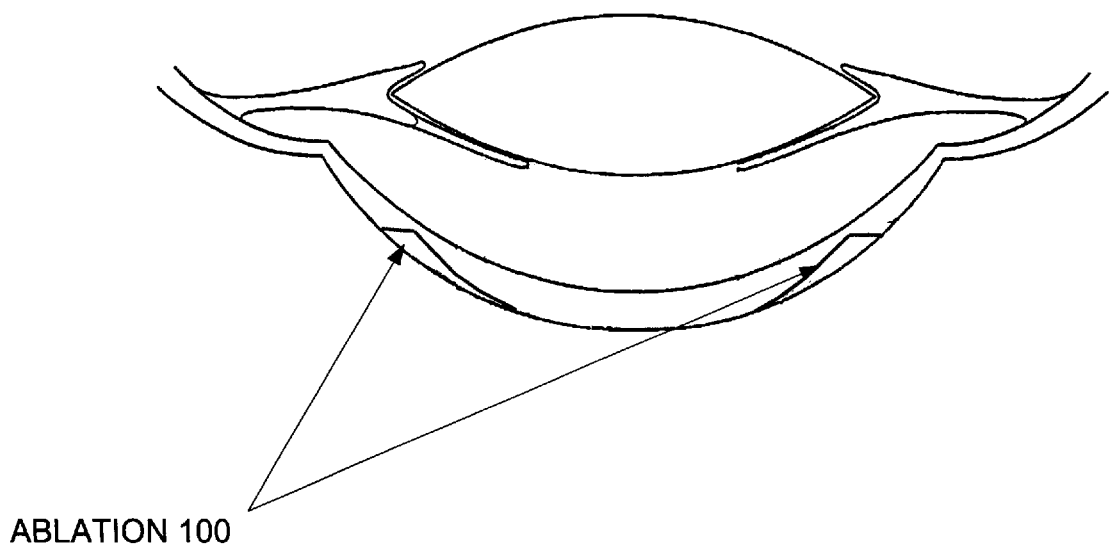
FIG. 5 shows a cross sectional view of an eye with a cornea that has undergone peripheral ablation in accordance with this invention.

FIG. 5 shows a cross sectional view of the eye with peripheral ablation 100 positioned in a peripheral zone of the cornea in accordance with the present invention.

In summary, using the method and apparatus described, a high refractive power peripheral cornea is produced by ablating a peripheral zone of the cornea extending from about 5.5 up to 10 mm or more without substantially changing the refractive power of a central zone of the cornea. The ablation steepens this peripheral zone to augment its dioptic power, thereby allowing the eye to focus on close objects without the use of a lens. During this process, the central zone of the cornea is not treated to insure that the distant vision remains unchanged. Since the central zone is not touched during the peripheral ablation required to treat presbyopia, it need not be covered or otherwise protected. After the peripheral ablation is completed, the central zone may be ablated in order to revert it to its characteristics prior to the peripheral ablation.

Numerous modifications may be made to this invention without departing from its scope as defined in the appended claims.

I claim:

1. A method of treating presbyopia in a patient comprising:
   peripherally ablating a peripheral zone of the cornea, said peripheral zone extending from about 5.5 to about 10 mm to form a high refractive power peripheral cornea to correct said presbyopia.

2. The method of claim 1 further comprising leaving said central portion of said cornea untreated to provide distant vision for the patient.

3. The method of claim 1 wherein during said peripheral ablation, the optical characteristics of said central zone of said cornea used for distant vision are changed, further comprising providing treatment to said central portion to revert said central portion so that its optical characteristics are similar to the characteristics prior to the peripheral ablation.

4. The method of claim 1 wherein said central zone has a diameter of about 5.5 mm.

5. The method of claim 1 further comprising changing the optical characteristics of said central zone of the cornea to correct said central zone for vision deficiencies other than near vision loss.

6. The method of claim 5 wherein said changing comprises performing ablation on said central zone.

7. A method of performing surgery on an eye with near vision deficiency comprising:
   determining the characteristics of the optical characteristics of the eye;
   determining a positive diopter correction for the eye;
   determining a peripheral ablation profile corresponding to said positive diopter correction; and
   performing a peripheral ablation on the cornea using said peripheral ablation profile while a central portion of the cornea remains untreated.

8. The method of claim 7 further comprising treating said central portion after said peripheral ablation.

9. The method of claim 8 wherein said treating includes correcting said central portion to revert said central portion to optical characteristics similar to its characteristics prior to the peripheral ablation.

10. The method of claim 8 wherein said eye suffers from other deficiencies further comprising treating said central portion to correct said other deficiencies.

11. The method of claim 1 wherein said peripheral ablation zone extends from about 5.5 mm to about 10 mm on the cornea.

* * * * *

UNITED STATES PATENT AND TRADEMARK OFFICE
CERTIFICATE OF CORRECTION

PATENT NO.      : 6,740,078 B2                                          Page 1 of 1
DATED           : May 24, 2004
INVENTOR(S)     : Tamayo It is certified that error appears in the above-identified patent and that said Letters Patent is hereby corrected as shown below:

Title page,
Item [76], Inventors, insert -- Mario G. Serrano, Calle 114 No. 9-45 Torre B Oficina 718, Bogota Columbia --

Signed and Sealed this

Twenty-first Day of December, 2004

JON W. DUDAS
*Director of the United States Patent and Trademark Office*